US00PP22867P2

(12) United States Plant Patent
Schimmelpfeng

(10) Patent No.: US PP22,867 P2
(45) Date of Patent: Jul. 24, 2012

(54) ***PRUNUS* PLANT NAMED 'WEIROOT 720'**

(50) Latin Name: *Prunus cerasus*
Varietal Denomination: Weiroot 720

(75) Inventor: Hermann Schimmelpfeng, Marzling (DE)

(73) Assignee: Technische Universität München, München (DE)

( * ) Notice: Subject to any disclaimer, the term of this patent is extended or adjusted under 35 U.S.C. 154(b) by 309 days.

(21) Appl. No.: 12/658,047

(22) Filed: Feb. 1, 2010

(51) Int. Cl.
*A01H 5/00* (2006.01)

(52) U.S. Cl. ..... Plt./183

(58) Field of Classification Search ..... Plt./183
See application file for complete search history.

(56) References Cited

OTHER PUBLICATIONS

UPOV ROM GTITM Computer Database GTI Jouve Retrieval Software 2011/10 Citation for 'Weiroot 720'.*

* cited by examiner

*Primary Examiner* — Wendy C Haas
(74) *Attorney, Agent, or Firm* — C. A. Whealy

(57) ABSTRACT

A new and distinct cultivar of *Prunus* plant named 'Weiroot 720', characterized by its upright plant habit; weak vegetative growth and low vigor; good soil adaptation; and as a rootstock, weak vegetative growth imparts uniformity, higher yield and larger fruit size to the scion plant.

3 Drawing Sheets

Botanical designation: *Prunus cerasus.*
Cultivar denomination: 'WEIROOT 720'.

BACKGROUND OF THE INVENTION

The present invention relates to a new and distinct cultivar of *Prunus* plant, typically used as a cherry tree rootstock, botanically known as *Prunus cerasus*, and hereinafter referred to by the name 'Weiroot 720'.

The new *Prunus* plant is a naturally-occurring whole plant mutation of *Prunus cerasus* 'Weiroot 72', not patented. The new *Prunus* plant was discovered and selected by the Inventor from within a population of plants of 'Weiroot 72' in the autumn of 2001 in an outdoor nursery in Bavaria, Freising, Germany.

Asexual reproduction of the new *Prunus* plant by tissue culture since the autumn of 2001 in a controlled environment in Bavaria, Freising, Germany has shown that the unique features of this new *Prunus* plant are stable and reproduced true to type in successive generations.

SUMMARY OF THE INVENTION

Plants of the new *Prunus* have not been observed under all possible environmental conditions. The phenotype may vary somewhat with variations in environment such as temperature and light intensity, without, however, any variance in genotype.

The following traits have been repeatedly observed and are determined to be the unique characteristics of 'Weiroot 720'. These characteristics in combination distinguish 'Weiroot 720' as a new and distinct cultivar of *Prunus:*

1. Upright plant habit.
2. Weak vegetative growth and low vigor.
3. Good soil adaptation.
4. As a rootstock, weak vegetative growth imparts uniformity, higher yield and larger fruit size to the scion plant.

Plants of the new *Prunus* plant differ primarily from plants of the parent, 'Weiroot 72', in the following characteristics:

1. Plants of the new *Prunus* root better than plants of 'Weiroot 72'.
2. Plants of the new *Prunus* have weaker vegetative growth than plants of 'Weiroot 72'.
3. Due to its weaker vegetative growth, plants of the new *Prunus* impart higher yield and larger fruit size to the scion plant than plants of 'Weiroot 72'.

Plants of the new *Prunus* can be compared to plants of *Prunus* 'Weiroot 158', not patented. In side-by-side comparisons conducted in Bavaria, Freising, Germany, plants of the new *Prunus* differed primarily from plants of 'Weiroot 158' in the following characteristics:

1. Plants of the new *Prunus* had weaker vegetative growth than plants of 'Weiroot 158'.
2. Due to its weaker vegetative growth, plants of the new *Prunus* imparted higher yield and larger fruit size to the scion plant than plants of 'Weiroot 158'.

BRIEF DESCRIPTION OF THE PHOTOGRAPHS

The accompanying photographs illustrate the overall appearance of the new *Prunus* plant. These photographs show the colors as true as it is reasonably possible to obtain in colored reproductions of this type. Colors in the photographs may differ slightly from the color values cited in the detailed botanical description which accurately describe the colors of the new *Prunus* plant.

The photograph on the first sheet comprises a side perspective view of a typical tree of 'Weiroot 720' grown in an outdoor orchard.

The photograph on the second sheet comprises a close-up view of a typical tree of 'Weiroot 720' grown in an outdoor orchard.

The photograph on the third sheet is a close-up view of a typical flowering branch of 'Weiroot 720'.

DETAILED BOTANICAL DESCRIPTION

The aforementioned photographs, following observations and measurements describe plants grown during the summer in Nederweert, The Netherlands in an outdoor nursery and under conditions and practices generally used in commercial *Prunus* production. Plants were one year old when the photographs and description were taken. Measurements and numerical values represent averages for typical plants and plant parts. The actual measurements of any individual plant or plant parts, or any group of plants or plant parts, of the new *Prunus* plant may vary from the stated average. In the following description, color references are made to The Royal Horticultural Society Colour Chart, 2001 Edition, except where general terms of ordinary dictionary significance are used.

Botanical classification: *Prunus cerasus* 'Weiroot 720'.

Parentage: Naturally-occurring whole plant mutation of *Prunus cerasus* 'Weiroot 72', not patented.

Propagation:

*Type*.—By cuttings.

*Time to initiate roots, summer*.—About eight weeks at 24° C.

*Time to initiate roots, winter*.—About 16 weeks at 24° C.

*Time to produce a rooted young plant, summer*.—About five months at 24° C.

*Time to produce a rooted young plant, winter*.—About eight to ten months at 24° C.

*Root description*.—Fibrous, woody; brown in color.

*Rooting habit*.—Moderate branching; moderately dense.

*Growth rate*.—After two years of growth, the root ball is about 1 meter deep and about 40 cm to 50 cm in diameter.

Plant description:

*Plant and growth habit*.—Used a rootstock; upright plant habit; plant are typically grown as a single stem; low vigor.

*Plant height*.—About 80 cm to 100 cm.

*Plant diameter*.—About 60 cm to 70 cm.

*Stem description*.—Strength: Strong. Texture: Smooth, glabrous. Color: Light green.

*Leaf description*.—Arrangement: Alternate; simple. Length: About 5 cm to 6 cm. Width: About 3 cm to 3.5 cm. Shape: Elliptic to ovate. Apex: Acuminate. Base: Cordate. Margin: Crenate. Texture, upper surface: Rough, glabrous. Texture, lower surface: Rough, pubescent. Venation pattern: Pinnate. Color: Developing and fully developed leaves, upper surface: Close to 143A; venation, close to 144B. Developing and fully developed leaves, lower surface: Close to 143B; venation, close to 144D. Petiole: Length: About 1 cm to 1.3 cm. Diameter: About 3 mm. Color, upper and lower surfaces: Close to 178A.

Flower description:

*Flower type/habit*.—Numerous single rotate flowers arranged on compound panicles; flowers face outwardly to slightly drooping; freely flowering habit; about 8 to 14 flowers per inflorescence; flowers not persistent.

*Fragrance*.—Faint, pleasant.

*Natural flowering season*.—Continuously flowering during the spring in The Netherlands.

*Flower buds*.—Height: About 1 cm to 2 cm. Diameter: About 5 mm to 10 mm. Shape: Oval to rounded. Color: Close to 155D.

*Inflorescence height*.—About 6 cm to 8 cm.

*Inflorescence diameter*.—About 12 cm to 15 cm.

*Flower diameter*.—About 2 cm to 3 cm.

*Flower depth*.—About 2 cm to 3 cm.

*Petals*.—Arrangement: Five petals in a single whorl. Length: About 8 mm to 15 mm. Width: About 5 mm to 10 mm. Shape: Obovate. Apex: Obtuse. Base: Cordate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement: Five sepals in a single whorl. Length: About 4 mm to 6 mm. Width: About 3 mm to 5 mm. Shape: Ovate to deltoid. Apex: Rounded. Base: Cordate. Margin: Entire. Texture, upper and lower surfaces: Smooth, glabrous. Color, upper and lower surfaces: Close to 185A.

*Pedicels*.—Length: About 2 mm to 4 mm. Diameter: About 1 mm to 2 mm. Angle: About 60° to 90° from the inflorescence stalk. Strength: Moderately strong. Texture: Smooth, glabrous. Color: Close to 144A.

*Reproductive organs*.—Stamens: Quantity per flower: Numerous. Filament length: About 5 mm to 8 mm. Filament color: Close to 154D. Anther length: About 2 mm to 4 mm. Anther color: Close to 6A. Pollen amount: Scarce. Pollen color: Close to 6D. Pistils: Quantity per flower: About six to eight. Pistil length: About 4 mm to 7 mm. Style length: About 3 mm to 6 mm. Style color: Close to 154A. Stigma shape: Round. Stigma color: Close to 6A.

*Seeds/fruits*.—Seed and fruit development have not been observed on plants of the new *Prunus*.

Temperature tolerance: Plants of the new *Prunus* have been observed to tolerate temperatures from about −20° C. to about 35° C.

It is claimed:

1. A new and distinct *Prunus* plant named 'Weiroot 720' as illustrated and described.

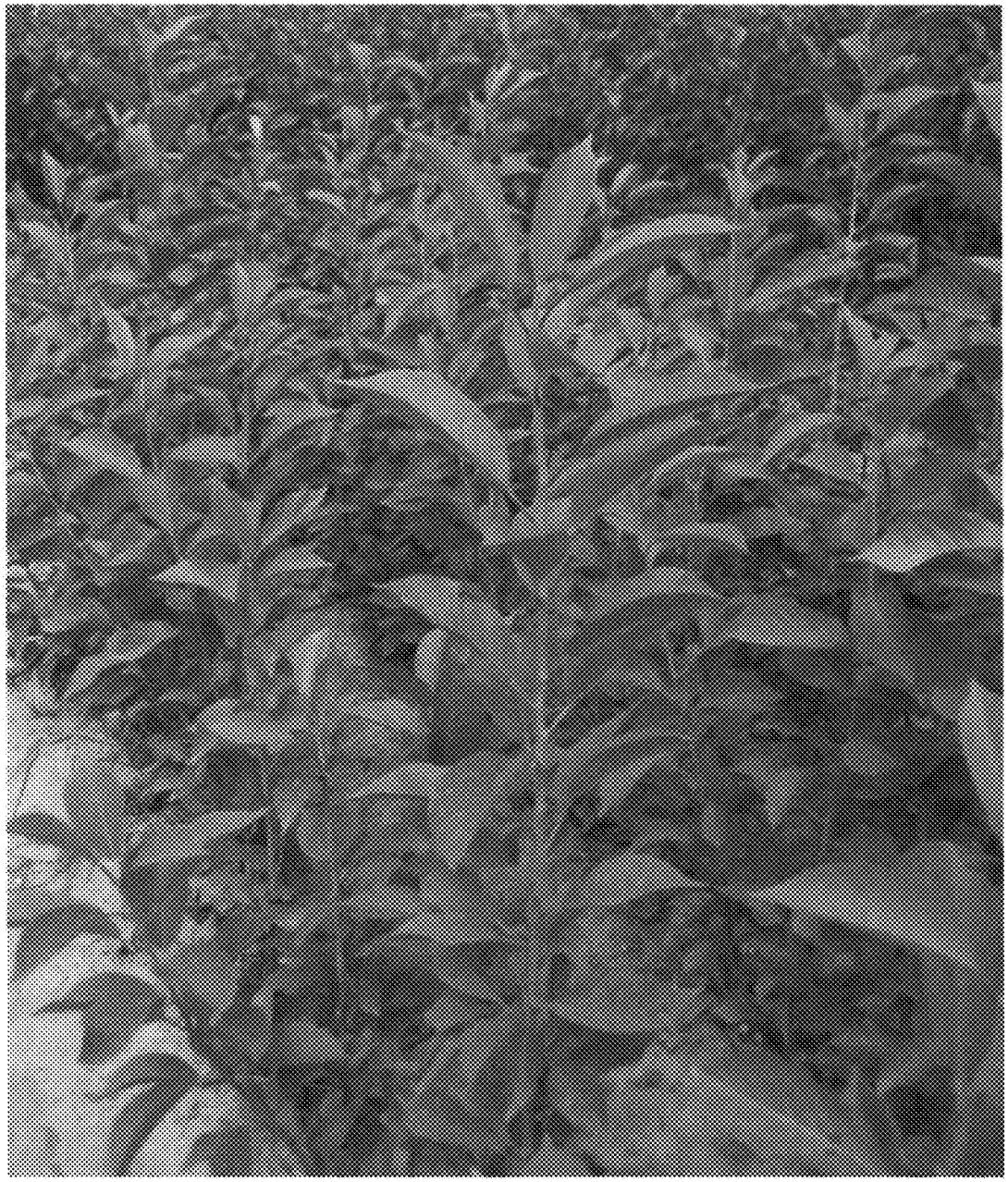

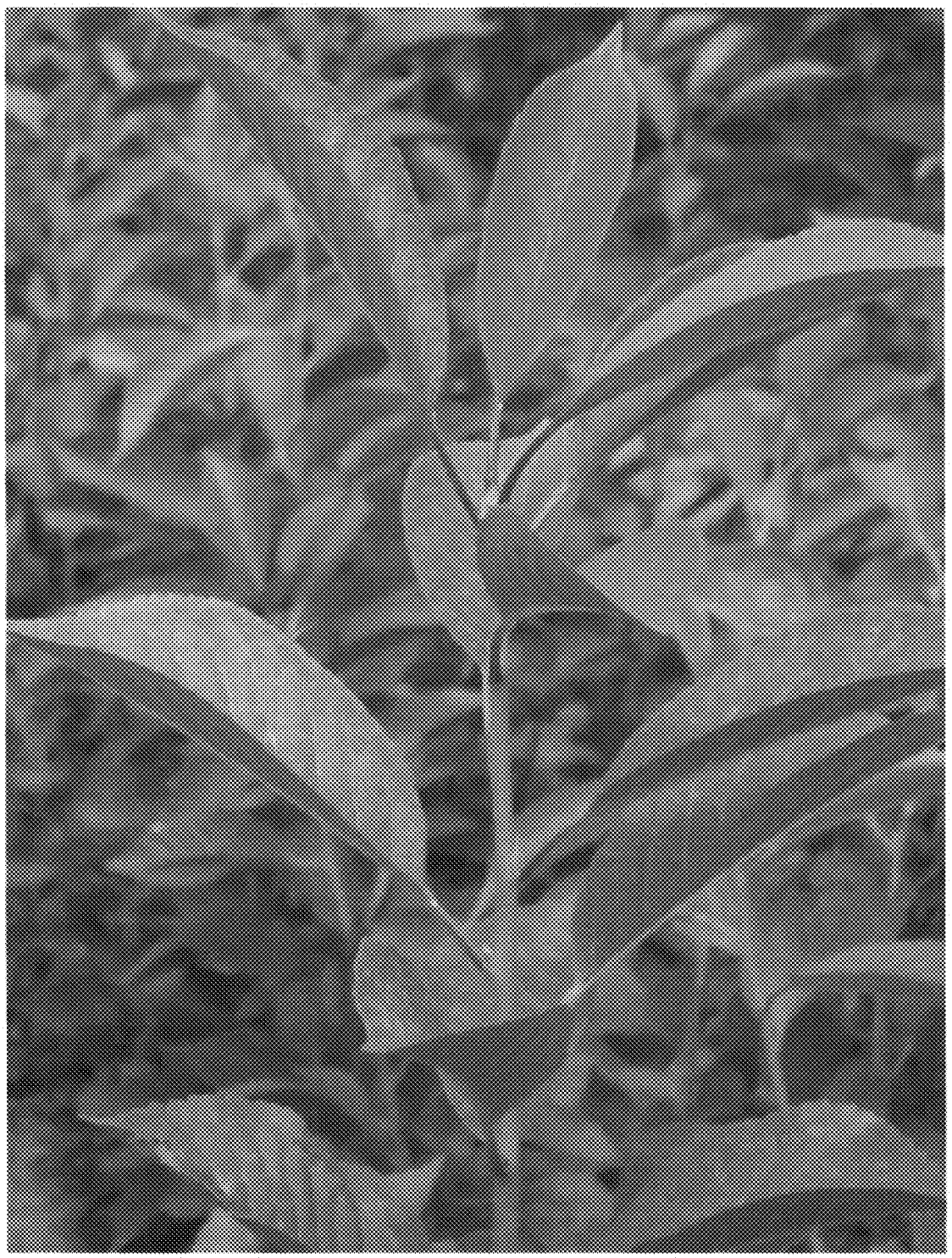

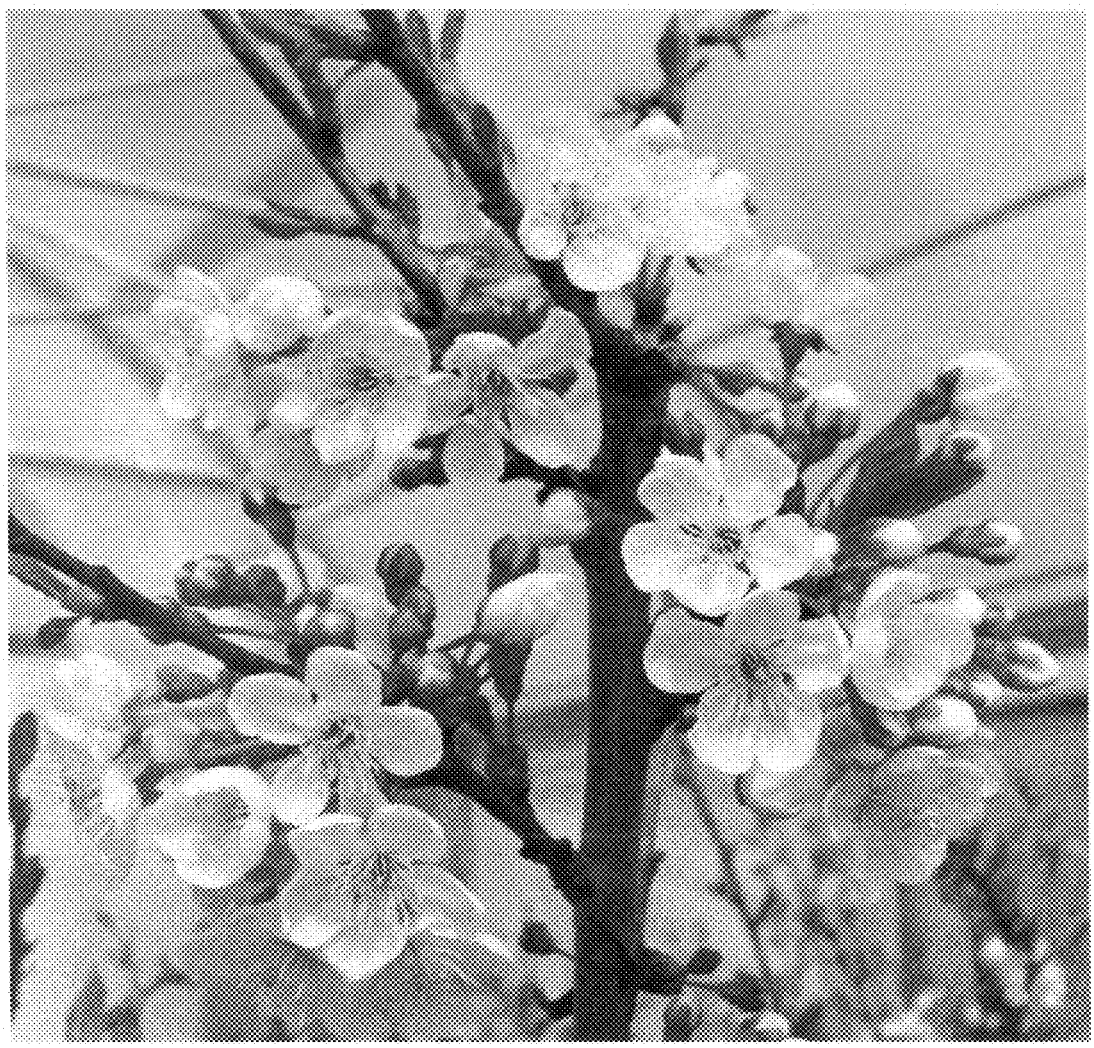

* * * * *